United States Patent [19]

Tagliabue et al.

[11] Patent Number: 4,774,320

[45] Date of Patent: Sep. 27, 1988

[54] SYNTHETIC PEPTIDE WITH HUMAN INTERLEUKIN 1 ACTIVITY

[75] Inventors: Aldo Tagliabue, Pianella; Guido Antoni, Castelnuovo Berardenga; Rivo Presentini, Siena; Diana Boraschi, Pianella, all of Italy

[73] Assignee: Sclavo S.p.A., Siena, Italy

[21] Appl. No.: 922,066

[22] Filed: Oct. 20, 1986

[30] Foreign Application Priority Data

Feb. 7, 1986 [IT] Italy ............... 19338 A/86

[51] Int. Cl.⁴ .............................. C07K 7/06
[52] U.S. Cl. ................... 530/328; 530/351; 514/885
[58] Field of Search ........... 530/351, 328; 514/2, 514/15

[56] References Cited

PUBLICATIONS

March et al, *Nature* 315, 1985, pp. 641–645.
Lomedico et al, *Nature* 312, 1985, pp. 458–462.
Auron et al, *PNAS* 81, 1984, pp. 7907–7911.
Cameron et al, *J. Exp. Med.* 162, 1985, pp. 790–801.
Hopp et al, *PNAS* 78, 1981, pp. 3824–3825.
Dinarello et al, *J. Immunol.*, 133, 9/1986, pp. 1332–1338.
Kack et al, *J. Exp. Med., 163, 1986, pp. 463–468.*
Rimsky et al, *J. Immunol.* 136(9) 1986, pp. 3304–3310.
Antoni et al, *J. Immunol.* 137(10) 1986, pp. 3201–3204.

*Primary Examiner*—John Kight
*Assistant Examiner*—Garnette D. Draper
*Attorney, Agent, or Firm*—Hedman, Gibson, Costigan & Hoare

[57] ABSTRACT

Synthetic peptide with human interleukin 1 activity, which peptide can be used as a stimulant of the immune functions and can be defined by the general formula:

Val-Gln-Gly-Glu-Glu-Ser-Asn-Asp-Lys-X        (I)

where: Val=L-valine; Gln=L-glutamine; Gly=glycine; Glu=L-glutamic acid; Ser=L-serine; Asn=L-asparagine; Asp=L-aspartic acid; Lys=L-lysine; X=cysteine (Cys), OH, NH$_2$, a benzyl ester or an alkyl ester group having a number of carbon atoms from 1 to 7.

5 Claims, 1 Drawing Sheet

SYNTHETIC PEPTIDE WITH HUMAN INTERLEUKIN 1 ACTIVITY

FIELD OF THE INVENTION

The present invention relates to a synthetic peptide with human interleukin 1 activity, which can be used as a stimulant of the immune functions.

The invention further relates to a process for the production of the said synthetic peptide with human interleukin 1 activity and to medicinal compositions containing at least an effective quantity of the said peptide.

BACKGROUND OF THE INVENTION

Human interleukin 1 (IL-1) is a protein having a molecular weight of 20,000–25,000 and belonging to the family of the lymphomonokines, a plentiful group of proteins which modulate the immune functions.

Human interleukin 1, which is produced to a large extent by cells of the monocyte/macrophage line, appears to be one of the most significant stimulants of the T lymphocytes (Oppenheim, J. J. et al., Fed. Proc. 41, 257 (1982)).

IL-1 does in fact appear to contribute to the amplification of the immune response during the phase of recognition of the antigen, this taking place by means of an effect on the helper T lymphocytes and on the cytotoxic T lymphocytes.

Furthermore, IL-1 appears to be capable of carrying out multiple actions which are not specifically immunological but which, nevertheless, because they take place in the course of inflammation, may be ascribed to a different mechanism of protection which the host utilizes in order to overcome pathological conditions.

Among the various proinflammatory activities of IL-1, we shall mention the induction of fever, the induction of prostaglandin $E_2$ and of proteins of the acute phase and the activation of neutrophils. Finally, IL-1 assists in the activation of repair mechanisms in the event of tissue damage, stimulating the growth of fibroblasts.

Having regard to its multiple activities, the possibility of using IL-1 as an immunomodulating drug has constantly become more attractive.

According to a process known in the art, interleukin 1 is produced by inducing secretion thereof by normal macrophages/monocytes of peripheral blood by means of the application of an inducing agent of bacterial origin.

However, this method presents difficulties such as the use of a large number of blood donors and a complex procedure for the separation of the monocytes.

French Patent Application No. 2,550,802 describes and claims a process for the production of interleukin 1 which comprises the culturing, in an appropriate culture medium, of a human leukemic cell line of haematopoietic origin and the induction of the secretion of interleukin 1 on the part of the said cells, by means of the application of inducing agents such as phorbols or esters thereof.

There then follows the separation of the interleukin 1 thus obtained from the culture medium and purification thereof by conventional methods. Nevertheless, this process is complicated by the numerous stages required and by the poor total yields, which reduce the attractiveness of the process itself from the industrial point of view.

There have recently been identified and cloned the genes which code for two proteins α and β with IL-1 activity (Lomedico, P. T. et al.: Nature 312, 641 (1985); Auron, P. E. et al.: Proc. Natl. Acad. Sci, USA: 81, 7907 (1984)); March, C. J. et al.: Nature 315, 641 (1985)).

The use of the said genes for the preparation of heterolqgous proteins by the recombinant DNA technique does however present numerous problems.

In fact, operating according to the said technique leads on the one hand to the necessity for an accurate assessment of the possible risks which are generally associated with the introduction, into human therapy, of products obtained by means of genetic manipulations, and on the other hand to a situation in which there are difficulties in the production and purification of the desired proteins.

It has now been found that it is possible to overcome the difficulties of the known technique by means of a synthetic peptide with human interleukin 1 activity, which peptide can be used as a stimulant of the immune functions and as an adjuvant in vaccines and can be obtained in a pure form by a process which is simple and economically convenient.

The object of the present invention is accordingly to provide a synthetic peptide with human interleukin 1 activity, which peptide can be used as a stimulant of the immune functions and as an adjuvant in vaccines.

A further object of the present invention is to provide a process for the preparation thereof.

A yet further object of the present invention is constituted by the use of the said peptide for the preparation of pharmaceutical compositions which can be used to stimulate and/or to restore immune responses and as an adjuvant in the preparation of vaccines. Still further objects of the present invention will become evident from the description of the text and of the experimental examples which follow.

SUMMARY OF THE INVENTION

In particular, the synthetic peptide according to the present invention can be defined by means of the following formula:

$$\text{Val-Gln-Gly-Glu-Glu-Ser-Asn-Asp-Lys-X} \qquad (I)$$

where:
- Val = L-valine
- Gln = L-glutamine
- Gly = glycine
- Glu = L-glutamic acid
- Ser = L-serine
- Asn = L-asparagine
- Asp = L-aspartic acid
- Lys = L-lysine
- X = cysteine (Cys), OH, $NH_2$, benzyl ester or an alkyl ester group having a number of carbon atoms from 1 to 7.

In accordance with the present invention we have identified the active site of the human IL-1 protein, the amino acid sequence of which, as inferred from the nucleotide sequence of the corresponding gene, is set forth below:

|     | 1   | 2   | 3   | 4   | 5   | 6   | 7   | 8   | 9   | 10  | 11  | 12  | 13  | 14  | 15  |
| --- | --- | --- | --- | --- | --- | --- | --- | --- | --- | --- | --- | --- | --- | --- | --- |
| 1   | MET | ALA | GLU | VAL | PRO | LYS | LEU | ALA | SER | GLU | MET | MET | ALA | TYR | TYR |
| 16  | SER | GLY | ASN | GLU | ASP | ASP | LEU | PHE | PHE | GLU | ALA | ASP | GLY | PRO | LYS |
| 31  | GLN | MET | LYS | CYS | SER | PHE | GLN | ASP | LEU | ASP | LEU | CYS | PRO | LEU | ASP |
| 46  | GLY | GLY | ILE | GLN | LEU | ARG | ILE | SER | ASP | HIS | HIS | TYR | SER | LYS | GLY |
| 61  | PHE | ARG | GLN | ALA | ALA | SER | VAL | VAL | VAL | ALA | MET | ASP | LYS | LEU | ARG |
| 76  | LYS | MET | LEU | VAL | PRO | CYS | PRO | GLN | THR | PHE | GLN | GLU | ASN | ASP | LEU |
| 91  | SER | THR | PHE | PHE | PRO | PHE | ILE | PHE | GLU | GLU | GLU | PRO | ILE | PHE | PHE |
| 106 | ASP | THR | TRP | ASP | ASN | GLU | ALA | TYR | VAL | HIS | ASP | ALA | PRO | VAL | ARG |
| 121 | SER | LEU | ASN | CYS | THR | LEU | ARG | ASP | SER | GLN | GLN | LYS | SER | LEU | VAL |
| 136 | MET | SER | GLY | PRO | TYR | GLU | LEU | LYS | ALA | LEU | HIS | LEU | GLN | GLY | GLN |
| 151 | ASP | MET | GLU | GLN | GLN | VAL | VAL | PHE | SER | MET | SER | PHE | VAL | GLN | GLY |
| 166 | GLU | GLU | SER | ASN | ASP | LYS | ILE | PRO | VAL | ALA | LEU | GLY | LEU | LYS | GLU |
| 181 | LYS | ASN | LEU | TYR | LEU | SER | CYS | VAL | LEU | LYS | ASP | ASP | LYS | PRO | THR |
| 196 | LEU | GLN | LEU | GLU | SER | VAL | ASP | PRO | LYS | ASN | TYR | PRO | LYS | LYS | LYS |
| 211 | MET | GLU | LYS | ARG | PHE | VAL | PHE | ASN | LYS | ILE | GLU | ILE | ASN | ASN | LYS |
| 226 | LEU | GLU | PHE | GLU | SER | ALA | GLN | PHE | PRO | ASN | TRP | TYR | ILE | SER | THR |
| 241 | SER | GLN | ALA | GLU | ASN | MET | PRO | VAL | PHE | LEU | GLY | GLY | THR | LYS | GLY |
| 256 | GLY | GLN | ASP | ILE | THR | ASP | PHE | THR | MET | GLN | PHE | VAL | SER | SER |     |

Auron, P. E. et al.: Proc. Natl. Acad. Sci., USA: 81, 7907 (1984).

It is known that the biological activity of a protein depends upon the interaction of the protein molecule with other substances present in the surrounding environment.

Accordingly, the active site of a protein will presumably be found in a zone of the molecule which is thoroughly exposed to the aqueous solvent.

The degree of exposure to the solvent of the various parts of the protein molecule may be assessed on the basis of the distribution of hydrophilic residues along the primary structure.

Such an assessment may be made by means of the use of various methods (Rose, G. D. et al., Proc. Natu. Acad. Sci. USA 77, 4643–4647 (1980); Kyte, J. et al., J. Mol. Biol. 157, 105–132 (1982). Hopp, T. P. et al., Proc. Nat. Acad. Sci. USA 78, 3824–3828 (1981)).

In particular, we operated in accordance with the method proposed by Hopp, T. P. et al. in "Synthetic Antigens" P. 47-60 Annuali Sclavo 1984, which makes use of a particular scale of hydrophilic properties, referred to as acrophilic properties, and which is particularly effective in individually identifying zones of the protein molecule which are exposed to the solvent.

The method consists in calculating, for each amino acid residue of the sequence in position (i), where (i) is intended to represent an integer which represents the position of the residue under examination within the sequence, the mean value of the acrophilic properties for 6 residues, from the position $i-2$ to the position $i+3$.

FIG. 1 shows the profile of acrophilic properties of human interleukin 1, starting from the residue in position 117.

The residues from 1 to 116 have not been analysed, since these are not present in the biologically active mature molecule. The profile of acrophilic properties determined by us in this manner shows numerous peaks, corresponding to zones of the molecule which are rich in hydrophilic residues.

In particular, it was possible to demonstrate a peak with a high degree of acrophilic properties corresponding to the 163–171 peptide segment.

In accordance with the present invention, we accordingly synthesized a peptide, hereinafter referred to as the 163–171-peptide, the amino acid sequence of which corresponds to that of the 163–171-peptide segment and a peptide modified by adding a cysteine residue to the 163–171-peptide in position 10.

The biological activity of the said synthetic peptides was then determined in accordance with the method described by Gery, I. et al.: J. Exp. Med. 136, 128 (1972).

The synthesis of the peptides (I) of the present invention may be carried out, in accordance with known methods, in the homogeneous phase or in the solid phase.

According to the present invention, peptides of formula (I) are prepared by means of a process which takes place in the solid phase and which comprises the steps of:

(a) condensing an amino acid protected at the α-amino group with an insoluble solid support, by means of an esterification reaction between its salified carboxyl group and the benzyl group of the solid support;

(b) removing the α-amino-protective group;

(c) condensing the amino acid bound to the insoluble solid support with a second amino acid protected at the α-amino group, by means of a reaction between the deprotected amino group of the first amino acid and the carboxyl group of the second amino acid;

(d) removing the α-amino-protective group from the second amino acid;

(e) introducing the amino acids, in successive stages, in accordance with the techniques set forth in steps b-d, until completion of the desired peptide chain;

(f) removing the peptide thus synthesized from the soluble solid support and purifying the same.

For each stage of the process set forth above, the solid support to which the growing peptide chain is bound is recovered by filtration and washing carefully in order to remove the soluble impurities.

Examples of solid supports used in the synthesis in the solid phase on the peptides of formula (I) are the following: polystyrene resins reticulated with divinylbenzene, phenolic resins and polyamide resins.

Use is preferably made of polystyrene resins reticulated with approximately 1% and 2% of divinylbenzene, activated with chloromethyl and with a final content of chlorine of approximately 1 milliequivalent per gram of resin.

On the resin activated in this manner, there is then condensed the C-terminal amino acid, expediently protected at the α-amino group, by means of an esterification reaction between the salified carboxyl group and the benzyl group present on the resin.

Protective groups for the α-amino group are selected from benzyloxycarbonyl, triphenylmethyl, t-amyloxycarbonyl, 2-nitrophenylsulphanyl, fluorenylmethyloxycarbonyl (Fmoc) and tert-butyloxycarbonyl (Boc).

Among these, particularly suitable for the purpose are the Fmoc and Boc groups, which can be removed under mild operating conditions.

According to the present invention, the Boc α-aminoprotective group was used.

The removal of the said protective group is generally carried out by means of treatment with a 50% solution of trifluoroacetic acid in $CH_2Cl_2$, at ambient temperature (20°–25° C.).

The reactive functional groups present in the side chains of the amino acids are generally protected by protective groups which are known in the synthesis of peptides.

Typically, use is made of protective groups which are stable under the conditions of removal of the α-aminoprotective group.

Protective groups which are particularly suitable for the purpose are the following: for lysine, the ortho-bromobenzyloxycarbonyl group (o-BrZ) or the benzyloxycarbonyl group (Z); for aspartic and glutamic acids, the benzyl ester group, for serine, the benzyl ether group and for cysteine, the 4-methylbenzyl group. The protective groups of the side chains are removed simultaneously with the detachment of the complete peptide from the resin.

At stage (a) of the present invention, the esterification reaction is carried out in the liquid phase, in an inert (non-reactive) organic solvent, in the presence of potassium iodide.

The operating temperatures are within the range between 30° C. and 60° C.

The operation is preferably carried out at a temperature of 50° C.

At stages (c) and (e) of the process of the present invention, the amino acids are introduced in the growing peptide chain, in the form of symmetric anhydrides.

Generally, the symmetric anhydrides are prepared by causing the appropriately protected amino acid and the dicyclohexylcarbodiimide (DCC) to react, in a liquid medium, in an inert organic solvent, at a temperature from −10° C. to +30° C.

In particular, the operation is carried out at a temperature of 0° C. for a period of time from 10 minutes to 30 minutes and then at ambient temperature (20°–25° C.) for a period of time from 5 minutes to 10 minutes.

The amino acids Asn and Gln are added to the resin as p-nitrophenyl esters.

In particular, the condensation reaction between the p-nitrophenyl esters and the resin is carried out in an inert organic solvent in the presence of an equimolar quantity of hydroxybenzotriazole.

Inert organic solvents which are suitable for this purpose are selected from chlorinated aliphatic hydrocarbons, dimethylformamide and dimethylacetamide.

In particular, $CH_2Cl_2$ is used as organic solvent.

On completion of the reaction for the synthesis of the peptide, in stage (f) the removal thereof from the solid support takes place by means of acidolytic or alkaline hydrolysis, aminolysis or alcoholysis.

The reaction is preferably carried out by acidolysis in accordance with known techniques.

Typically, the procedure is carried out by suspending the peptide-resin in anisole and the suspension which is obtained is cooled to a temperature equal to or approximately equal to −70° C.

Anhydrous hydrofluoric acid is thus caused to condense, the agitated suspension.

The temperature is then brought to within the range from −10° C. to +10° C., and the suspension is maintained at the said temperature for a period of time such as is necessary to bring the reaction to completion or almost to completion.

The peptide (I) obtained in this manner is dissolved in acidic aqueous solvent and is then purified by chromatography.

The fractions containing the peptide are then recovered and freeze-dried.

The biological activity of the peptides obtained in this manner was tested by means of the test described by Gery, I. et al. in J. Exp. Med. 136, 128 (1972).

The results which are obtained show that the said peptides are capable of reproducing the activity of the entire molecule of human IL-1, promoting the production of IL-2 and, consequently, the proliferation of immuno-competent cells.

Thus, these peptides may be used for the preparation of pharmaceutical compositions which can be used for stimulating and/or restoring immune responses and as adjuvants in the preparation of vaccines.

The experimental examples which follow are illustrative and do not restrict the invention.

Figure 1:
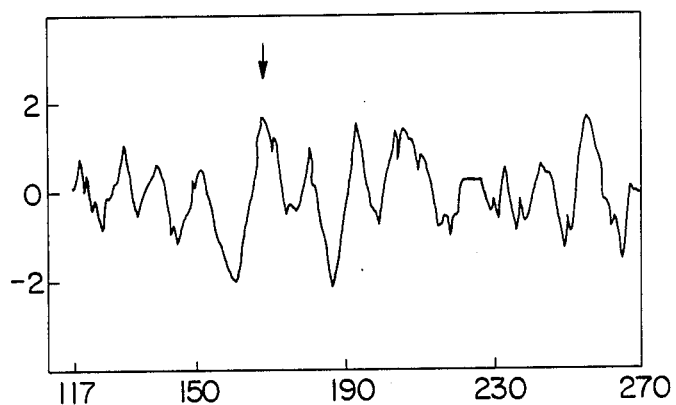
FIG. 1 shows the profile indicating the acrophilic properties of human IL-1 based on the amino acid residue in position 117.

The shaded lower part represents the proliferation of thymocytes in the presence of phytohaemagglutinin (PHA); the upper shaded part represents the activity of human IL-1 in a purified condition (diluted 1:20). The ordinate shows the proliferation of thymocytes expressed in the form of a count per minute (cpm) $\times 10^{-3}$, and the abscissa shows the concentration of (PHA, human IL-1) and of the peptide 163–171 expressed in μg/ml.

EXAMPLE 1

Synthesis of the peptide
Val-Gln-Gly-Glu-Glu-Ser-Asn-Asp-Lys-OH

The synthesis of the peptide is carried out, in the solid phase, with the use of a Beckmann synthesizer, model 990, and, as insoluble solid support, a copolymer of polystyrene and 1% divinylbenzene (Fluka) chloromethylate, having a content of residual chlorine of 1 milliequivalent per gram of resin.

(a) Introduction of Boc-Lys (oBrZ)-OH onto the resin.

5.75 g (12.5 mmol) of Boc-Lys (oBrZ)-OH are dissolved in 25 ml of ethanol.

The solution is adjusted to pH 7.0 with a 0.5M solution of caesium bicarbonate, and then the solvent is evaporated to dryness under vacuum. The residue obtained in this manner is absorbed in anhydrous dioxane and again evaporated to achieve complete removal of the water, and is then dried over $P_2O_5$.

The residue, 5 g of chloromethylated resin and 133 mg of KI are placed in a glass flask having a capacity of 100 ml and containing 40 ml of dimethylformamide (DMF). The resulting suspension is maintained at 50° C. for 48 hours, with gentle agitation.

At the conclusion of the said period, the resin is separated by filtration and washed as follows: 3 times with 50 ml, in each instance, of DMF; 3 times with 50 ml of a solution DMF:H$_2$O (1:1, V/V); 50 ml of water; 50 ml of glacial acetic acid, 50 ml of water and finally with 50 ml of absolute ethyl alcohol.

The resin is dried under vacuum over P$_2$O$_5$ (0.1 mm Hg, for approximately 2 hours).

The resin exhibits a lysine content of 0.55 mmol/g of resin.

(b) Introduction of the aspartic acid.

1.455 g of Boc-Lys(oBrZ)-resin, obtained as stated under (a) is treated in succession with the following reagents:

15 ml of CH$_2$Cl$_2$ for 30 minutes; 15 ml of CH$_2$Cl$_2$ for 2 minutes, on 3 occasions; 15 ml of 55% trifluoroacetic acid (TFA) (V/V) in CH$_2$Cl$_2$ for 15 minutes; 15 ml of CH$_2$Cl$_2$ for 2 minutes on 2 occasions; 15 ml of 25% dioxane (V/V) in CH$_2$Cl$_2$ for 2 minutes on 6 occasions. 2.4 mmol of symmetric anhydride of Boc-Asp (oBZ-)OH in 15 ml of CH$_2$Cl$_2$ are then condensed with the terminal amino group of the lysine attached to the resin by esterification.

The condensation reaction is carried out at ambient temperature (20°-25° C.); until such time as a sample of resin analysed by means of the ninhydrin test (Kaiser, E., et al. Anal. Biochem. 34, 395 (1970), gives a negative result.

At the end of the said period, the resin is separated from the reaction mixture and is washed with 15 ml of CH$_2$Cl$_2$ (for 2 minutes, on 3 occasions) and with 15 ml of 33% ethanol (EtOH) in CH$_2$Cl$_2$ (V/V) (for 2 minutes, on 3 occasions).

There then follows the introduction, in individual steps and in accordance with the desired sequence, of the appropriately protected amino acids, this procedure being carried out as stated above.

The amino acids Asn and Gln are introduced in the form of p-nitrophenyl esters.

2.4 mmol of the p-nitrophenyl ester of the amino acid are dissolved in 15 ml of CH$_2$Cl$_2$, in the presence of an equimolecular quantity of hydroxybenzotriazole and placed to react with the resin. The reaction is carried out at ambient temperature, with mild agitation, for approximately 12 hours, until such time as the ninhydrin test gives a negative result.

The quantity of the amino acids, the reaction period and the solvents employed are shown in the table which follows.

TABLE 1

| Amino acids | g | mmol | Solvents | Reaction period | Remarks |
|---|---|---|---|---|---|
| Asp | 1.55 | 4.8 | CH$_2$Cl$_2$ | 30–60 min. | |
| Asn | 1.13 | 3.2 | " | 12 hours | introduced in the form of p-nitrophenyl ester |
| Ser | 1.417 | 4.8 | " | 30–60 min. | |
| Gln | 1.618 | 4.8 | " | 30–60 min. | |
| Glu | 1.618 | 4.8 | " | " | |
| Gly | 0.84 | 4.8 | " | " | |
| Glu | 1.17 | 3.2 | " | 12 hours | introduced in the form of p-nitrophenyl ester |
| Val | 1.042 | 4.8 | " | 30–60 min. | |

The symmetric anhydrides are synthesised at the time of use, operating in the following manner.

4.8 mmol of protected amino acid are dissolved in 5 ml of CH$_2$Cl$_2$, and the solution is cooled to 0° C.

4 ml of 0.6 M dicyclohexylcarbodiimide (DCC) in CH$_2$Cl$_2$ are then added to this solution.

The resulting mixture is maintained at 0° C., with gentle agitation, for 15 minutes.

The solution is then brought to ambient temperature (20°-25° C.), filtered on a porous glass disc and washed with CH$_2$Cl$_2$ so as to reach a final volume of 15 ml of solution.

(c) Detachment of the peptide from the resin.

0.57 g (0.2 mmol) of peptide-resin obtained as stated under stage b) is placed in a Teflon container having a capacity of 50 ml, and 1 ml of anisole is then added. The solution is brought to a temperature of −70° C., and 10 ml of anhydrous HF are added during a period of approximately 5 minutes.

The mixture is then maintained, under agitation, at −15° C. for 30 minutes and at 0° C. for 30 minutes. At the end of this period, anhydrous HF is removed from the reaction mixture by means of a stream of nitrogen, washed with 15 ml of cold anhydrous ethyl ether on 3 occasions, to eliminate the impurities, and finally with 5 ml of 0.5 M acetic acid on 3 occasions in order to extract the reaction product. The combine acid extracts are then brought to dryness under vacuum. A detachment efficiency of 95% is obtained.

(d) Purification of the peptide

The crude peptide obtained in this manner is dissolved in 5 ml of 0.5 M CH$_3$COOH, and the solution is purified by chromatography using a Sephadex G-10 column (2.5×90 cm) calibrated in 0.5 M CH$_3$COOH.

The fractions containing the peptide are identified by reaction with 2,4,6-trinitrobenzenesulphonic acid (TNBS) in accordance with the method of Mokrasch et al. Anal. Biochem. 18, 64 (1967).

The said fractions are then combined, freeze-dried and dissolved in 4 ml of 0.1% aqueous TFA and purified by chromatography (HPLC) in 2 aliquot parts of 2 ml each, using a Perkin-Elmer C-18 column (2×27.5 cm) calibrated in 0.1% TFA, with a flow rate of 10 ml/minute, and with a concave gradient from 0 to 100% of CH$_3$OH in 0.1% TFA.

The fractions containing the peptide, individually identified by analysis of the absorption at 210 nm in a Perkin-Elmer LC-75 apparatus, are collected and brought to dryness under vacuum.

The product obtained is then dissolved in 5 ml of 0.01 M NH$_4$HCO$_3$ and subjected to chromatography using a Sephadex G-10 column (2.5×50 cm) calibrated in NH$_4$HCO$_3$.

The fractions containing the peptide were individually identified by analysis with Folin-Lowry reagent in accordance with the report given in J. Biol. Chem. 193, 265 (1951), collected and freeze-dried. The product obtained is 126 mg of pure peptide, with a yield of 63% calculated with respect to the quantity of the first amino acid bound to the resin.

The product was identified by analysis of the amino acids after hydrolysis with 6 N HCl in a closed phial at 110° C. for 24 hours.

Values obtained as residues analysed:

Theoretical: Asx 2.00; Ser 1.00; Glx 3.00; Gly 1.00; Val 1.00; Lys 1.00.

Found: Asx 2.02; Ser 1.02; Glx 2.94; Gly 1.00; Val 0.97; Lys 1.05.

Asx=Asp+Asn; Glx=Glu+Gln.

EXAMPLE 2

Synthesis of the peptide Val-Gln-Gly-Glu-Glu-Ser-Asn-Asp-Lys-Cys-OH

The synthesis of the peptide is carried out by a procedure as stated in Example 1 hereinabove, by attaching to the resin by esterification in step a) 4.06 g (12.5 mmol) of Boc (4-methylbenzyl-cysteine).

The resin has a cysteine content of 0.6 mmol/g of resin.

EXAMPLE 3

Tests on the activity of stimulation of the immune system by the peptide Val-Gln-Gly-Glu-Glu-Ser-Asn-Asp-Lys-OH (a) Proliferation of thymocytes.

The activity of the peptide was determined by testing the costimulation of thymocytes obtained from inbred C3H/HeJ mice (not responsive to bacterial endotoxin) of 4-5 weeks, according to the method reported by Gery, I. et al. (J. Exp. Med. 136, 128, 1972).

The test consists in culturing for 72 hours at 37° C., in 5% of $CO_2$, 0.2 ml of RPMI 1640 medium containing 5% of bovine foetal serum, in the presence of submitogenic doses of phytohaemagglutinin (PHA). To a batch of thymocytes activated subliminally by PHA, there are then added increasing doses of the peptide 163–171 (50–100–200–400–800 µg/ml) and to the remaining batch of thymocytes a purified human IL-1B standard (Genzyme Boston Mass.).

Figure 2:
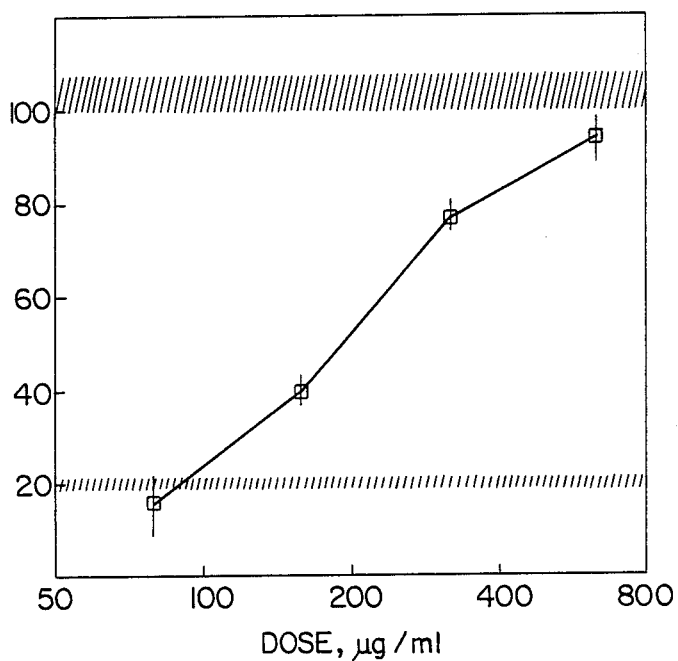
FIG. 2 shows the proliferation of thymocytes induced by the peptide 163–171 (□)

The proliferation of the thymocytes is then measured by means of a beta scintillator based on the quantity of tritiated thymidine incorporated in the nucleus of the proliferating cells. As is evident from FIG. 2, it is found that the synthetic peptide 163–171 (□) possesses a significant activity of costimulation of the murine thymocytes.

(b) Induction of the production of IL-2 on the part of the synthetic peptide.

In the test of Gery I., the human interleukin 1 acts not as a growth factor of the thymocytes themselves, but stimulates their proliferation by means of induction of the production of interleukin-2 (IL-2) in a sub-population of T lymphocytes present in the thymus. IL-2 produced in this manner subsequently promotes the proliferation of the thymocytes themselves.

For the purpose of establishing whether the activity of costimulation of the murine thymocytes on the part of the synthetic peptide is due, as in the case of human IL-1, to the induction of the production of IL-2, the following test was carried out.

T cells from the spleen of C3H/HeJ mice, separated on nylon wool as reported by Julius, M. H. et al., Eur. J. Immunol. 3, 645 (1973), are incubated in duplicate for 48 hours at 37° C. in 1 ml of RPMI 1640 medium (GIBCO), supplemented by N-2-hydroxyethylpiperazine N'-2-ethanesulphonic acid (HEPES), L-glutamine, gentamycin, 10% bovine foetal serum and 2-mercaptoethanol ($2.5 \times 10^{-5}$ M), in the presence of graduated concentrations (840–420–210 µg/ml) of the synthetic peptide 163–171 and of purified human IL-1B as standard, with the addition of concanavalin A (ConA) as costimulant.

At the end of the period of incubation, the supernatant is separated from the culture and a determination is made of its capacity to promote the growth of CTLL-2 cells dependent upon IL-2 according to the method reported by Gillis S. M. et al. (J. Immunol. 120, 2027 (1978)).

The mitogenic activity of IL-2 on CTLL-2 cells is measured, either by determining the number of cells after 24 hours of culturing or by means of the assessment of the incorporation of tritiated thymidine in the cells. It can be seen from the results reported in Table 2 given below, that the synthetic peptide 163–171 is capable of stimulating the production of IL-2 by T cells of the spleen activated by ConA to a greater extent than that of purified human IL-1B.

TABLE 2

Capacity of the peptide 163–171 to induce IL-2

| Experimental group | Dilution or conc. in µg/ml | Stimulation index + SE of CTLL cells | (mU/ml) |
|---|---|---|---|
| Medium | | 1.00 ± 0.12 | 1 |
| Human IL-1β | 1/10 | 0.93 ± 0.02 | 1 |
| Peptide 163–171 | 840 | 0.96 ± 0.11 | 1 |
| " | 420 | 1.03 ± 0.48 | 1 |
| " | 210 | 1.18 ± 0.23 | 1 |
| Supernatants of splenocytes incubated with ConA and: | | | |
| Medium | | 6.00 ± 0.20 | 3 |
| Human IL-1β | 1/10 | 15.27 ± 0.88 | 38 |
| Peptide 163–171 | 840 | 149.40 ± 4.65 | 721 |
| | 630 | 122.80 ± 11.43 | 586 |
| | 420 | 72.07 ± 3.43 | 444 |

Murine splenocytes were incubated for 48 hours in 5% $CO_2$ at 37° C. with the substances under investigation, and the supernatants collected for the purpose of incubation were tested for the capacity to induce proliferations of CTLL cells dependent on IL-2.

On the basis of these results, we can thus conclude that the peptide 163–171 is capable of reproducing the activity of the entire molecule of human IL-1, promoting the production of IL-2 and, in consequence, the proliferation of immunocompetent cells.

I claim:

1. A synthetic peptide having human interleukin 1 activity and being useful as a stimulant of the immune system, said peptides having the formula:

Val-Gln-Gly-Glu-Glu-Ser-Asn-Asp-Lys-X     (I)

wherein Val is L-valine; Gln is L-glutamine; Gly is glycine; Glu is L-glutamic acid; Ser is L-serine; Asn is L-asparagine; Asp is L-aspartic acid; Lys is L-Lysine; and X is selected from L-cysteine (Cys), OH, NH₂, a benzyl ester and an alkyl ester having from 1 to 7 carbon atoms.

2. The synthetic peptide of claim 1, having the formula:

Val-Gln-Gly-Glu-Glu-Ser-Asn-Asp-Lys-OH.

3. The synthetic peptide of claim 1 having the formula:

Val-Gln-Gly-Glu-Glu-Ser-Asn-Asp-Lys-NH₂.

4. The synthetic peptide of claim 1 having the formula:

Val-Gln-Gly-Glu-Glu-Ser-Asn-Asp-Lys-Cys.

5. A pharmaceutical composition comprising a therapeutically effective amount of the synthetic peptide of claim 1 in combination with a pharmaceutically acceptable carrier.

* * * * *